United States Patent [19]

Iwahara

[11] Patent Number: 4,952,736

[45] Date of Patent: Aug. 28, 1990

[54] PROCESS FOR PRODUCING ALKOXYALKYL GROUP SUBSTITUTED PHENOLS

[75] Inventor: Masahiro Iwahara, Tokuyama, Japan

[73] Assignee: Idemitsu Petrochmeical Company, Limited, Tokyo, Japan

[21] Appl. No.: 469,724

[22] Filed: Jan. 24, 1990

Related U.S. Application Data

[63] Continuation of 217,921 filed as PCT JP 87/00832 on Oct. 29, 1987, Published as WO 88/03129 on May 5, 1988, abandoned.

[30] Foreign Application Priority Data

Oct. 30, 1986 [JP] Japan ............................ 61-259366
Nov. 6, 1986 [JP] Japan ............................ 61-264195

[51] Int. Cl.$^5$ ............................................. C07C 41/00
[52] U.S. Cl. ................................... 568/628; 568/662
[58] Field of Search ............................... 568/628, 662

[56] References Cited

U.S. PATENT DOCUMENTS 2,841,623 7/1958 Morton et al. ................... 568/485
4,633,022 12/1986 Greco ................................ 568/660

FOREIGN PATENT DOCUMENTS 60-500260 2/1985 Japan.

Primary Examiner—Bruce Gray
Attorney, Agent, or Firm—Armstrong, Nikaido, Marmelstein, Kubovcik & Murray

[57] ABSTRACT

This invention is a process for production of an alkoxyalkyl group substituted phenol represented by the following formula (1) in high yields and at high selectivity:

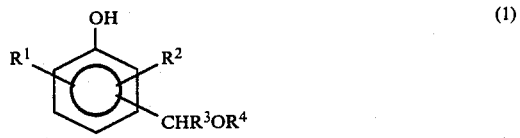

wherein $R^1$, $R^2$ and $R^3$ each represents a hydrogen atom or an alkyl group; and $R^4$ represents an alkyl group by reacting a phenol, an alcohol and an aldehyde in the presence of a catalyst selected from the group consisting of a tertiary alkylamine, a tertiary unsubstituted benzylamine, a mixture of a tertiary alkylamine and a tertiary unsubstituted benzylamine, a carbonate of alkali metal, a hydrogencarbonate of alkali metal and a mixture of a carbonate of alkali metal and a hydrogencarbonate of alkali metal, and recovering said alkoxyalkyl substituted phenol from said reaction product.

24 Claims, 3 Drawing Sheets

PROCESS FOR PRODUCING ALKOXYALKYL GROUP SUBSTITUTED PHENOLS

This application is a continuation of application Ser. No. 217,921 filed as PCT JP87/00832 on Oct. 29, 1987, published as WO88/03/29 on May 5, 1988, now abandoned.

TECHNICAL FIELD

This invention relates to a process for producing alkoxyalkyl group substituted phenols represented by the formula (1):

(wherein $R^1$, $R^2$ and $R^3$ each represents a hydrogen atom or an alkyl group and $R^4$ represents an alkyl group). More particularly, it relates to a process for producing alkoxyalkyl group substituted phenols according to which alkoxyalkyl group substituted phenols used as antioxidants, preservatives and starting materials for other chemicals can be produced in high yields and the objective product can be easily separated from catalysts.

BACKGROUND ART

As antioxidants, preservatives and starting materials for other chemicals, there are generally known alkoxyalkyl group substituted phenols such as, for example, 2,6-di-t-butyl-4-methoxymethylphenol.

Hitherto, there have been many processes for producing the alkoxyalkyl group substituted phenols.

For example, a process is known which comprises reacting a phenol such as 2,6-di-t-butylphenol, an alcohol and formaldehyde in the presence of a tertiary amine derived from phenols such as, for example, N,N-dimethyl-3,5-di-t-butyl-4-hydroxybenzylamine (Mannich base).

However, yield obtained by this process is about 82% and is not satisfactory. Besides, since the objective product and the catalyst are similar in their structure, separation from each other is not easy.

It is also known to react a phenol such as 2,6-di-t-butylphenol, an alcohol and formaldehyde in the presence of a hydroxide of alkali metal to produce an alkoxyalkyl group substituted phenol.

However, yield of alkoxyalkyl group substituted phenol in this process is low of less than about 50%.

U.S. Pat. No. 2,838,571 discloses a process for production of alkoxyalkyl group substituted phenols by reacting a 2,6-dialkylphenol, formaldehyde and an alcohol in the presence of a metallic hydroxide.

However, yield of alkoxyalkyl group substituted phenols according to this process is also unsatisfactory.

On the other hand, U.S. Pat. No. 4,633,022 filed on Sept. 16, 1985 in U.S.A. and issued on Oct. 30, 1986 discloses a process for producing a bisether represented by the formula (A):

which is different from the objective alkoxyalkyl group substituted phenols of this invention by reaction of a 2,6-dialkyl substituted phenol with formaldehyde in methyl alcohol in the presence of a tertiary amine.

According to the process disclosed in the above U.S. Pat. No. 4,633,022, the bisether represented by the above formula can be obtained by reacting a 2,6-dialkyl substituted phenol with formaldehyde in methanol in the presence of a tertiary amine under inert gas atmosphere.

However, tracing experiments by the present inventors repeating examples given in U.S. Pat. No. 4,633,022 has revealed that the bisether claimed in U.S. Pat. No. 4,633,022 cannot be produced by the process disclosed in U.S. Pat. No. 4,633,022.

That is, in utterly the same manner as in Example 1 of U.S. Pat. No. 4,633,022, 206 g (1 mol) of 2,6-di-t-butylphenol, 500 ml of methanol, 36 g (1 mol) of paraformaldehyde and 125 ml (0.9 mol) of triethylamine were refluxed under nitrogen stream of 1 atm at 70° C. over a period of 16 hours.

The reaction mixture was subjected to atmospheric distillation to remove 250 ml of a mixture of methanol and triethylamine and the residue was cooled to 25° C.

Crystal separated by this cooling was filtered, washed with 50 ml of methanol five times and then dried.

Yield of the resulting crystal was 157.5 g (Yield is 233 g according to the disclosure of U.S. Pat. No. 4,633,022).

Figure 1:
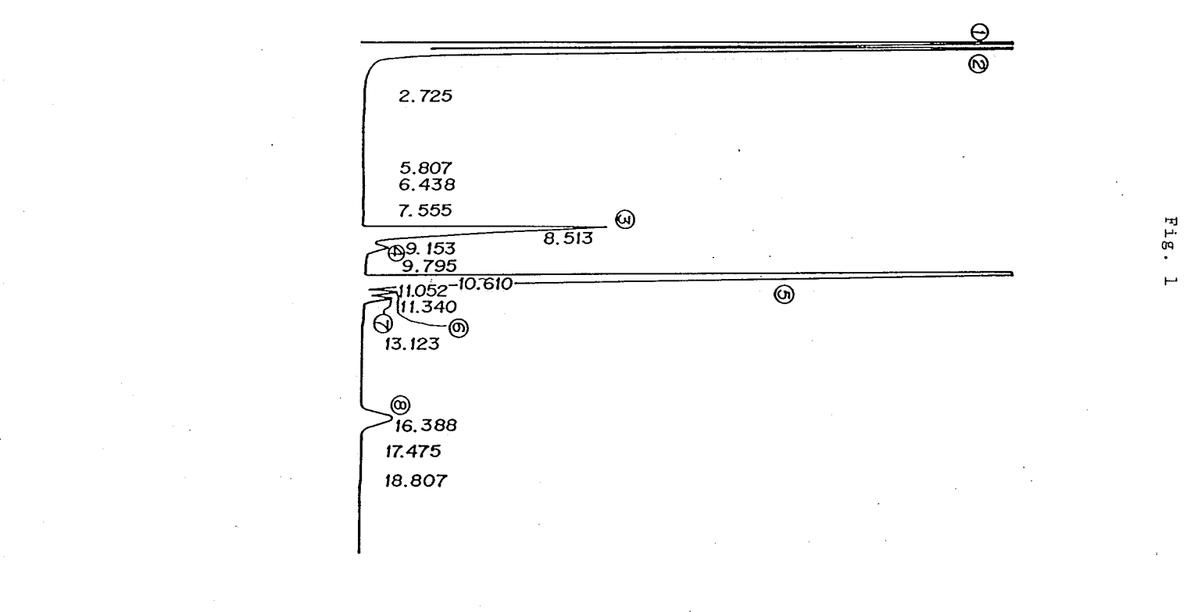
FIG. 1 is a GC chart which shows the results of tracing experiments of Example 1 of U.S. Pat. No. 4,633,022 which were conducted by the present inventors.

The crude crystal separated after the atmospheric distillation was analyzed by gas chromatography to obtain the GC analysis chart as shown in FIG. 1. Conditions of the gas chromatography are shown below.

GC analytical device: SHIMAZU GC-9A (Shimazu Seisakusho, Ltd.)

FID

Column: 2 m

Packing material: Dexsil 300GC Uniport HP

Injection temperature: 250° C.

Column temperature: 70°–250° C.

Heating rate of column: 10° C./1 min for 70°–150° C.; 25° C./1 min for 150°–250° C.

Carrier gas: Nitrogen

As shown in FIG. 1, 8 peaks were found in the GC analysis chart as a result of gas chromatography analysis.

Substances given said 8 peaks were analyzed in GC-MS analysis to be identified as the compounds represented in Table 1. The yield of these compounds were represented in Table 1. analysis are as follows.

GC-MS analytical device

Conditions of GC are same as above

Conditions of MS: HITACHI M80B type double focusing mass spectrometer (Hitachi Limited)

Ionization voltage: 70 eV

Accelerating voltage: 3 KV

Ion source temperature: 200° C.

Scanning speed: 1–500 n/z (sec)

TABLE 1

| Peak NO. | Products | Yield (mol %) |
|---|---|---|
| (1) | Methanol | |
| (2) | Triethylamine | |
| (3) | 2,6-di-t-butylphenol | |
| (4) | 2,6-di-t-butyl-p-cresol | 2.5 |
| (5) | 2,6-di-t-butyl-4-methoxymethylphenol | 74.5 |
| (6) | 2,6-di-t-butyl-4-hydroxymethylphenol | 2.1 |
| (7) | 2,6-di-t-butyl-4-hydroxymethoxymethylphenol | 1.8 |
| (8) | 4,4'-Methylene-bis-(2,6-di-t-butylphenol) | 2.5 |

In this case, conversion rate of all products was 79.8% based on 2,6-di-t-butylphenol.

The present inventors have doubted if there are errors in the results of their tracing experiments of Example 1 of U.S. Pat. No. 4,633,022 and they carried out hydrogenation decomposition of the principal product (product shown by peak (5)) obtained by the above GC analysis in the presence of a catalyst. If the product shown by the peak (5) is the bisether disclosed in Example 1 of U.S. Pat. No. 4,633,022, trisubstituted phenol and water should be produced as shown in the following reaction formula (B).

Figure 2:
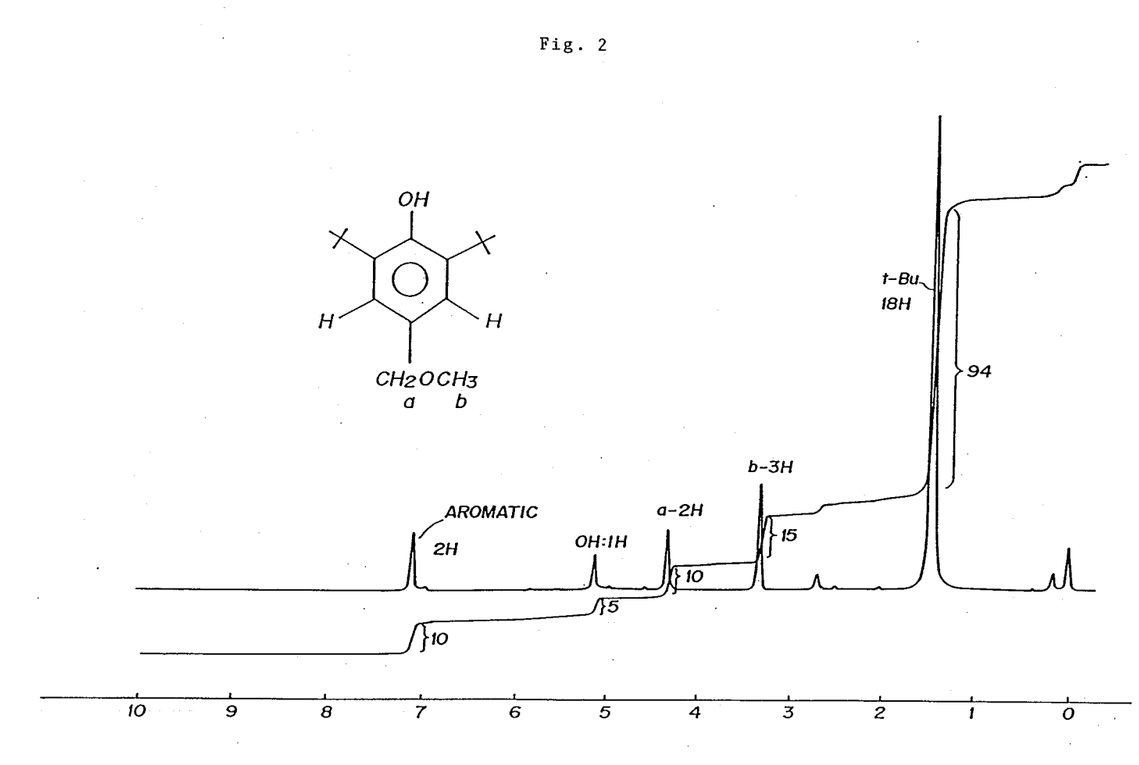
FIG. 2 is a $^1$H-NMR chart of 2,6-di-t-butyl-4-methoxymthylphenol.

However, according to the experiments conducted by the present inventors, BHT and methyl acetate were produced, although acetic acid was used as a solvent. From the results, it is reasonable to consider that in Example 1 of U.S. Pat. No. 4,633,022, bisether as shown by the formula (A) was not produced, but 2,6-di-t-butyl-4-methoxymethylphenol was produced. Moreover, $^1$H-NMR analysis of the product indicated by the peak (5) showed that said product was 2,6-di-t-butyl-4-methoxymethylphenol as shown in FIG. 2. Results of elemental analysis of the product shown by the peak (5) are as follows.

| Elements | Found | Calculated |
|---|---|---|
| C | 76.52 | 76.75 |
| H | 10.66 | 10.47 |

Thus, it was supported that the product was 2,6-di-t-butyl-4-methoxymethylphenol.

Therefore, it has been clarified by the present inventors that according to the process disclosed in U.S. Pat. No. 4,633,022, not bisether, but 2,6-di-t-butyl-4-methoxymethylphenol is produced as a principal product.

Moreover, according to Example 3 shown as a comparative example in U.S. Pat. No. 4,633,022, use of sodium hydroxide in place of triethylamine as catalyst in Example 1 resulted in reduction of yield to 58%. However, U.S. Pat. No. 2,838,571 and J. Am. Chem. Soc., 5019 (1957) disclose that when 2,6-di-t-butylphenol, methanol and paraformaldehyde are reacted using sodium hydroxide as a catalyst, 2,6-di-t-butyl-4-methoxymethylphenol is produced.

As mentioned above, the invention described in U.S. Pat. No. 4,633,022 does not disclose technical facts. Therefore, the invention described in U.S. Pat. No. 4,633,022 cannot be prior art.

Even if U.S. Pat. No. 4,633,022 can be prior art, this U.S. Pat. No. 4,633,022 discloses bisetherification reaction of two molecules of 2,6-dialkyl substituted phenol and this bisetherification reaction is against scientific fact as explained hereabove.

This invention has been made under such circumstances.

The object of this invention is to provide a process for production of alkoxyalkyl group substituted phenols in high yields where the objective product and catalyst can be easily separated.

DISCLOSURE OF INVENTION

As a result of the inventors' intensive research in order to accomplish the above object, it has been found that when an alcohol, a phenol and an aldehyde are allowed to react in the presence of a specific tertiary amine or carbonate or hydrogencarbonate of an alkali metal, an alkoxyalkyl group substituted phenol which is utterly different from the product disclosed in U.S. Pat. No. 4,633,022 can be produced in high yields and besides, the objective product and the catalyst can be easily separated and the recovered catalyst can be used as it is. This invention is based on this finding.

That is, the outline of this invention for attaining the above object is a process for producing an alkoxyalkyl group substituted phenol represented by the formula (1):

(1)

(wherein $R^1$, $R^2$ and $R^3$ each represents a hydrogen atom or an alkyl group and $R^4$ represents an alkyl group) by reacting a phenol, an alcohol and an aldehyde in the presence of a catalyst selected from the group consisting of a alkylamine, a tertiary unsubstituted benzylamine, a mixture of a tertiary alkylamine and a tertiary unsubstituted benzylamine, a carbonate of an alkali metal, a hydrogencarbonate of an alkali metal and a mixture of a carbonate of an alkali metal and a hydrogencarbonate of an alkali metal.

In this invention, a reaction utterly different from the reaction disclosed in U.S. Pat. No. 4,633,022 takes place. That is, one molecule of phenol, one molecule of alcohol and one molecule of aldehyde react to produce the alkoxyalkyl group substituted phenol represented by the above formula (1). Besides, according to this invention, the alkoxyalkyl group substituted phenol can be produced at high conversion rate and selectivity and in high yields.

Moreover, since in this invention, tertiary alkylamine and/or tertiary unsubstituted benzylamine which are not similar in structure to the objective alkoxyalkyl group substituted phenol are used as catalyst, separation between the catalyst and the alkoxyalkyl group substituted phenol can be easily performed.

Further, in this invention, the catalyst can be used repeatedly and thus this invention is also industrially useful in this regard.

BEST MODE FOR CARRYING OUT THE INVENTION

The tertiary amine used in this invention can be represented by the formula (2):

(2)

(wherein $R^5$, $R^6$ and $R^7$ each represents an alkyl group of 1-20 carbon atoms and $R^5$, $R^6$ and $R^7$ may be identical or different).

As the tertiary amine, mention may be made of, for example, N,N-diethyl-laurylamine, N,N-diethyl-tridecylamine, N,N-diethyl-palmitylamine, N,N-ethyl-dihexylamine, N-methyl-dipalmitylamine, trimethylamine, triethylamine, tripropylamine, tributylamine, tripentylamine, trihexylamine, triheptylamine, trioctylamine, trinonylamine, tricaprylamine, trilaurylamine, trimyristylamine, tricetylamine, tristearylamine and triarachylamines.

These various tertiary alkylamines may be used alone or in combination of two or more.

Among these tertiary alkylamines, preferred are those having lower alkyl groups of 1-4 carbon atoms as $R^5$, $R^6$ and $R^7$ such as trimethylamine, tripropylamine, tributylamine, N,N-dimethyl-ethylamine, N,N-dimethyl-propylamine, N,N-dimethyl-butylamine, N,N-diethyl-methylamine, N,N-diethyl-propylamine, N,N-diethyl-butylamine, N,N-dipropyl-ethylamine, N,N-dipropyl-butylamine, N,N-dibutyl-methylamine, N,N-dibutyl-ethylamine and N,N-dibutyl-propylamine. Especially preferred are those having the same lower alkyl group as $R^5$, $R^6$ and $R^7$ such as triethylamine and tributylamine.

The tertiary unsubstituted benzylamine can be represented by the formula (3):

(3)

(wherein $R^8$ and $R^9$ which may be identical or different each represents an alkyl group of 1-20 carbon atoms).

As the tertiary unsubstituted benzylamine, mention may be made of, for example, N-methyl-N-ethylbenzylamine, N-methyl-N-propylbenzylamine, N-methyl-N-butylbenzylamine, N-ethyl-N-propylbenzylamine, N-ethyl-N-butylbenzylamine, N-propyl-N-butylbenzylamine, N,N-dimethylbenzylamine, N,N-diethylbenzylamine, N,N-dipropylbenzylamine, N,N-dibutylbenzylamine, N,N-dipentylbenzylamine, N,N-dihexylbenzylamine, N,N-diheptylbenzylamine, N,N-dioctylbenzylamine, N,N-dinonylbenzylamine, N,N-dicaprylbenzylamine, N,N-dilaurylbenzylamine, N,N-dimyristylbenzylamine, N,N-benzyldicetylamine, N,N-distearylbenzylamine and N,N-diarachylbenzylamine. Among them, the tertiary unsubstituted benzylamines where $R^8$ and $R^9$ are same lower alkyl group of 1-20 carbon atoms are preferred and N,N-diethylbenzylamine and N,N-dibutylbenzylamine are especially preferred.

These tertiary unsubstituted benzylamines may be used alone or in combination of two or more.

In the process for production of phenols having alkoxyalkyl group according to this invention, either one of the tertiary alkylamine or the tertiary unsubstituted benzylamine can be used alone or they can be used in combination.

The carbonates and hydrogencarbonates of alkali metals include, for example, lithium carbonate, lithium hydrogencarbonate, sodium hydrogencarbonate, cesium carbonate, cesium hydrogencarbonate, rubidium carbonate, rubidium hydrogencarbonate and potassium sodium carbonate.

Among these carbonates or hydrogen carbonates of alkali metals, carbonate or hydrogencarbonates of sodium or potassium are preferred and especially preferred is at least one selected from sodium carbonate, sodium hydrogencarbonate and potassium carbonate.

The phenols used in this invention can be represented by the formula (4):

(4)

(wherein $R^1$ and $R^2$ each represents a hydrogen atom or an alkyl group of 1-12 carbon atoms and $R^1$ and $R^2$ may be identical or different).

As examples of these phenols, mention may be made of phenol, o-cresol, m-cresol, p-cresol, ethylphenol, propylphenol, p-tert-butylphenol, p-tert-amylphenol, o-sec-amylphenol, p-octylphenol, o-octylphenol, xylenol, p-nonylphenol, o-nonylphenol, 2,6-diisopropylphenol, 2,6-di-t-butylphenol, di-tert-amylphenol and di-sec-amylphenol.

Among them, preferred are those which have an alkyl group of 1-4 carbon atoms as $R^1$ and $R^2$ which are identical and especially preferred is 2,6-di-tert-butylphenol.

As the alcohols used in this invention, mention may be made of, for example, methyl alcohol, ethyl alcohol, n-propyl alcohol, isopropyl alcohol, n-butyl alcohol, isobutyl alcohol, sec-butyl alcohol, t-butyl alcohol, pentanol, pentanol-1, pentanol-2, pentanol-3, 2-methylbutanol-1, 2-methylbutanol-2, 2-methylbutanol-3, 2-methylbutanol-4, dimethylpropanol, hexanol-1, hexanol-2, heptanol-1, heptanol-2, octanol-1, octanol-2, 4-ethylhexanol-4, 2-ethylhexanol-1, nonanol-1, nonanol- 2, nonanol-3, decanol-1, decanol-2, undecanol-1, undecanol-2, dodecanol-1, tridecanol-1, tridecanol-2, tetradecanol-1, tetradecanol-2, pentadecanol-1, pentadecanol-2, hexadecanol-1, hexadecanol-2, heptadecanol-1, heptadecanol-2, octadecanol-1, octadecanol-2, nonadecanol-1, nonadecanol-2, eicosanol-1, eicosanol-2, heneicosanol, docosanol, tricosanol, tetracosanol, pentacosanol, hexacosanol, heptacosanol, octacosanol, nonacosanol, triacontanol, hentriacontanol, dotriacontanol, allyl alcohol, crotyl alcohol, 2-butenol-1, 2-pentenol-1, 3-hexenol-1, 2-heptenol-1, 10-undecenol-1, 11-dodecenol-1, 12-tridecenol-1, oleyl alcohol, elaidyl alcohol, linoleyl alcohol, linolenyl alcohol, ethylene glycol, diethylene glycol, triethylene glycol, propylene glycol, glycerin and Among these alcohols, those which are represented by the formula $R^4OH$ (wherein $R^4$ represents an alkyl group, preferably an alkyl group of 1–10 carbon atoms, more preferably 1–4 carbon atoms) are preferred and methyl alcohol is especially preferred.

As the aldehydes used in this invention, mention may be made of, for example, formaldehyde, paraformaldehyde, acetaldehyde, propionaldehyde, n-butylaldehyde, isobutylaldehyde, metacrolein, ethoxyacetaldehyde, n-valeroaldehyde, isovaleroaldehyde, methylethylaldehyde, trimethylacetaldehyde, n-hexaaldehyde, diethylacetaldehyde, dimethylethylacetaldehyde, 2-cyclopentenylacetaldehyde, ethyl-n-butylacetaldehyde, enanthoaldehyde, acrolein, crotonaldehyde, hydroxyaldehyde, salicylaldehyde, anisaldehyde and vanillin.

Among them, aldehydes represented by the formula $R^3CHO$ (wherein $R^3$ represents a hydrogen atom or an alkyl group of 1–12 carbon atoms) are preferred and paraformaldehyde is especially preferred.

In the process for producing alkoxyalkyl group substituted phenols according to this invention, phenol, alcohol and aldehyde are allowed to react in the presence of a catalyst selected from the group consisting of a tertiary amine, a tertiary unsubstituted benzyl amine, a mixture of a tertiary alkylamine and a tertiary unsubstituted benzylamine, a carbonate of an alkali metal, a hydrogencarbonate of an alkali metal and a mixture of a carbonate of an alkali metal and a hydrogencarbonate of an alkali metal.

The above catalyst may be either one of the tertiary amine or the tertiary unsubstituted benzylamine or a mixture thereof, either one of the carbonate of alkali metal or the hydrogencarbonate of alkali metal or a mixture thereof.

In this invention, the above reaction can be shown, for example, by the following reaction formula.

(wherein $R^1$, $R^2$, $R^3$ and $R^4$ have the same meanings as defined above).

The fact that the above reaction proceeds to give an alkoxyalky group substituted phenol cannot be easily known from U.S. Pat. No. 4,633,022 which does not disclose technical facts.

In the above reaction, solvents can be used.

As the solvents, alcohols represented by the formula $R^4OH$ which are also reactants in the reaction can be used.

Therefore, it is preferred to add the alcohol $R^4OH$ in an amount of large excess relative to the phenol in the above reaction.

Amount of the aldehyde relative to the phenol is 1–6 mols, preferably 2–4 mols per 1 mol of the phenol.

When amount of the aldehyde is less than 1 mol, sometimes the reaction does not proceed and even when more than 6 mols of the aldehyde is used, yield of the alkoxyalkyl group-containing phenol does not always increase.

When tertiary alkyl amine and/or tertiary unsubstituted benzylamine are used as catalyst, amount thereof is 1/200–1 mol, preferably 1/100–1/5 mol per 1 mol of phenol. When carbonate of alkali metal and/or hydrogencarbonate of alkali metal are used as catalyst, amount thereof is 1/300–1/5 mol, preferably 1/200–1/10 mol per 1 mol of phenol.

For all of these catalysts, when amount thereof is less than the above ranges, function of the catalyst is not sufficiently developed and thus, sufficient results cannot be obtained with reference to yield and when amount thereof is more than the above ranges, increase of yield corresponding to the amount is not always expectable.

The reaction is normally carried out at a reaction temperature of 0°–200° C., preferably 20°–150° C. When it is lower than 0° C., yield of the objective product is low and industrial operation becomes difficult to continue in actual production and when higher than 200° C., sometimes the catalytic action cannot be sufficiently exhibited.

Reaction pressure is within the range of 0–200 kg/cm$^2$.G, preferably 0–100 kg/cm$^2$.G. In this case, if the pressure is lower than 0 kg/cm$^2$.G, reaction does not proceed at sufficient velocity and yield does not increase and when more than 200 kg/cm$^2$.G, activity of the reaction may not be sufficiently increased.

Reaction time is normally 0.5–20 hours, preferably 1–10 hours. If the time is shorter than 0.5 hours, phonols having alkoxyalkyl groups is not sufficiently produced and even if it exceeds 20 hours, yield does not increase and sometimes the productivity decreases.

The reaction can be carried out in eather homogeneous or heterogeneous system.

When lithium hydrogencarbonate, sodium hydrogencarbonate, lithium carbonate or sodium carbonate is used as catalyst, the reaction will be in heterogeneous system and when potassium hydrogencarbonate, cesium hydrogencarbonate, potassium carbonate, cesium carbonate, tertiary amine or tertiary unsubstituted benzylamine is used, the reaction will be an homogeneous system.

Figure 3:
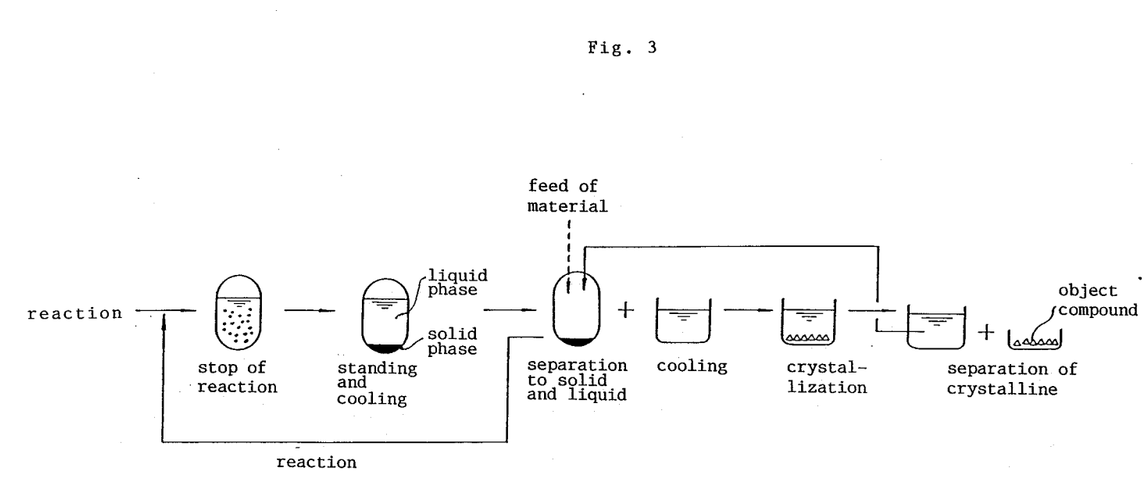
FIG. 3 is a flow chart which shows steps of after-treatment after completion of the reaction in this invention.

In case of reaction in a heterogeneous system, preferably the treatments as shown in FIG. 3 are effected after the reaction.

That is, after termination of the reaction, the reaction system is left to stand to cause separation into a liquid phase and a solid phase. Then, these are separated from each other, the resulting liquid phase is cooled, for example, to 0°–20° C. to crystallize the reaction product alkoxyalkyl group substituted phenol and the crystal is separated. To the solid phase obtained by the above separation into liquid and solid phases are added reaction starting materials such as phenols, alcohols and aldehydes and solvent solution (normally an alcohol which is a starting material) and the reaction of this invention is carried out again with this mixture.

In the case of homogeneous system, the reaction mixture after termination of the reaction is left to stand and simultaneously cooled, for example, to 0°–20° C. to crystallize the reaction product alkoxyalkyl group substituted phenol and the crystal is separated. The reaction product can be isolated by the crystal separation. Since the catalyst is dissolved in the resulting residue solution, starting materials are further added to the solution and the reaction of this invention is carried out. It is also possible to decompose the objective product by distillation.

The process of this invention can be carried out by batchwise or semibatchwise or continuous method and these may be optionally combined depending on industrial scale.

EXAMPLE 1

In an autoclave of 250 ml were charged 120 mmols of 2,6-di-tert-butylphenol, 100 ml of methanol, 200 mmols of paraformaldehyde and 30 mmols of triethylamine and reaction was conducted at 125° C., under 6 kg/cm$^2$.G for 3 hours.

After termination of reaction, the reaction mixture was cooled to 40° C. and conversion and selectivity were determined by gas chromatography. The results are shown in Table 1.

EXAMPLE 2

The solution after termination of reaction in Example 1 was cooled to 25° C. and phenol having alkoxyalkyl group was separated by filtration as a crystal. The filtrate was put in an autoclave of 250 ml and furthermore, 2,6-di-tert-butylphenol, methanol and paraformaldehyde were supplemented so that amounts of them reached 120 mmols, 100 ml and 200 mmols, respectively and then reaction was conducted. The results are shown in Table 1.

EXAMPLE 3

Example 2 was repeated except that the solution after termination of the reaction in Example 2 was used in place of the solution after termination of reaction in Example 1.

The results are shown in Table 1.

EXAMPLE 4

Example 2 was repeated except that the solution after termination of the reaction in Example 3 was used in place of the solution after termination of the reaction in Example 1. The results are shown in Table 1.

EXAMPLE 5

Example 2 was repeated except that the solution after termination of the reaction in Example 4 was used in place of the solution after termination of reaction in Example 1.

The results are shown in Table 1.

EXAMPLE 6

Example 1 was repeated except that trinormalbutylamine was used in place of triethylamine and reaction temperature was 100° C. and reaction pressure was 2 kg/cm$^2$.G.

The results are shown in Table 1.

EXAMPLE 7

Example 6 was repeated except that benzyldiethylamine was used in place of trinormal butylamine and reaction temperature was 125° C. and reaction pressure was 6 kg/cm$^2$.G.

The results are shown in Table 1.

COMPARATIVE EXAMPLE 1

A solution obtained by dissolving 500 mmols of 2,6-di-t-butylphenol in 50 ml of methanol, 220 ml of methanol, 800 mmols of paraformaldehyde and 3.0 g of 40% dimethylamine were charged in an autoclave of 1 liter and after addition in dropwise at 68° C. over a period of 3 hours, reaction was effected at 80° C. for 4 hours.

After termination of the reaction, conversion and selectivity were determined by gas chromatography.

The results are shown in Table 1.

As is clear from Table 1, when the conventionally used N,N-dimethyl-3,5-di-tert-butyl-4-hydroxybenzylamine was used as catalyst, both the conversion and the selectivity were lower than those in Examples 1–11.

TABLE 1

|  |  | Example |  |  |  |  |  |  | Comparative Example |
|---|---|---|---|---|---|---|---|---|---|
|  |  | 1 | 2 | 3 | 4 | 5 | 6 | 7 | 1 |
| Phenol (mmol) | 2,6-di-t-butylphenol | 120 | 120 | 120 | 120 | 120 | 120 | 120 | 500 |
| Alcohol (ml) | Methanol | 100 | 100 | 100 | 100 | 100 | 100 | 100 | 270 |
| Aldehyde (mmol) | Paraformaldehyde | 200 | 200 | 200 | 200 | 200 | 200 | 200 | 800 |
| Catalyst (mmol) | Triethylamine | 30 | 30 | 30 | 30 | 30 | — | — | — |
|  | Trinormalbutylamine | — | — | — | — | — | 30 | — | — |
|  | N,N-diethylbenzylamine | — | — | — | — | — | — | 30 | — |
|  | N,N-dimethyl-3,5-di-t-hydroxybenzylamine | — | — | — | — | — | — | — | 27 |
| Temperature (°C.) |  | 125 | 125 | 125 | 125 | 125 | 100 | 125 | 65/80 |
| Pressure (kg/cm$^2$G) |  | 6 | 6 | 6 | 6 | 6 | 2 | 6 | 0.6 |
| Time (hr) |  | 3 | 3 | 3 | 3 | 3 | 3 | 6 | 3/4 |
| Conversion of phenol (mol %) | Conversion of 2,6-di-t-butylphenol | 100 | 100 | 100 | 99 | 98 | 100 | 98 | 95 |
| Selectivity of phenol | Selectivity of 2,6-di-t- | 91 | 90 | 89 | 88 | 87 | 93 | 90 | 84 |

TABLE 1-continued

| | | Example | | | | | | | Comparative Example |
|---|---|---|---|---|---|---|---|---|---|
| | | 1 | 2 | 3 | 4 | 5 | 6 | 7 | 1 |
| containing alkoxyalkyl group (mol %) | butylmethoxy-metylphenol | | | | | | | | |

EXAMPLES 8, 9 AND 11 AND COMPARATIVE 10

EXAMPLES 2 AND 3

In 300 liter flask were charged phenol, alcohol and aldehyde in the amounts as shown in Table 2 and reaction was effected under the conditions as shown in Table 2 (reaction pressure of 0 kg/cm$^2$.G was not shown).

After termination of reaction, the reaction mixture was cooled to 25° C. A portion thereof was sampled and conversion and selectivity were determined by gas chromatography.

Results are shown in Table 2.

EXAMPLE 10

As shown in FIG. 2, the solution after termination of reaction obtained in Example 8 was left to stand to cause separation into a liquid phase and a solid phase.

Then, after separation of the solid and liquid phases, the resulting liquid phase was cooled to 0°-20° C. to crystallize the reaction product phenol containing alkoxyalkyl group and the crystal was separated. To the solid phase obtained by the separation in solid and liquid phases were added starting materials such as phenol, alcohol and aldehyde and solvent solution (normally, alcohol which is a starting material) obtained after separation of the crystal to obtain the ratio as shown in Table 2 and reaction of this invention was again carried out.

After termination of the reaction, the reaction mixture was cooled to 25° C. and then, a portion was sampled and conversion and selectivity were determined by gas chromatography.

The results are shown in Table 2.

As is clear from Table 2, according to this invention, alkoxyalkyl group substituted phenol were produced at sufficiently high conversion and selectivity (at high yield).

TABLE 2

| | | Example | | | | Comparative Example | |
|---|---|---|---|---|---|---|---|
| | | 8 | 9 | 11 | 11 | 2 | 3 |
| Phenol (mmol) | 2,6-di-t-butylphenol | 0.12 | 0.12 | 0.12 | 0.12 | 1.0 | 0.12 |
| Alcohol (ml) | Methanol | 150 | 150 | 150 | 150 | 7.5 (mol) | 150 |
| Aldehyde (mmol) | Paraformaldehyde | 0.3 | 0.3 | 0.3 | 0.3 | 1.06 (Formalin) | 0.3 |
| Catalyst (g) | Na$_2$CO$_3$ | 3 | — | (3) | — | — | — |
| | NaHCO$_3$ | — | 3 | — | — | — | — |
| | K$_2$CO$_3$ | — | — | — | 3 | — | — |
| | NaOH | — | — | — | — | Water 0.66 mol adjusted to pH 9.0 | — |
| | KOH | — | — | — | — | — | 1 |
| Temperature (°C.) | | 60 | 60 | 60 | 60 | 45 | 45 |
| Time (hr) | | 2 | 2 | 2 | 1 | 1 | 4 |
| Conversion of phenol (mol %) | Conversion of 2,6-di-t-butylphenol | 99 | 98 | 98 | 99 | 29 | 75 |
| Selectivity of phenol containing alkoxyalkyl group (mol %) | Selectivity of 2,6-di-t-methoxybutyl-4-methoxy-methylphenol | 92 | 89 | 91 | 91 | 90 | 77 |

[INDUSTRIAL APPLICABILITY OF THE INVENTION]

As explained above, according to the process of this invention, alkoxyalkyl group substituted phenols can be obtained at high conversion and selectivity and in high yield by reaction of phenols, alcohols and aldehydes and besides, catalyst can be repeatedly reused. Thus, this is an economical process which is industrially advantageous.

I claim:

1. A process for production of an alkoxyalkyl group substituted phenol, characterized by producing an alkoxyalkyl group substituted phenol represented by the formula (1):

(1)

wherein $R^1$, $R^2$ and $R^3$ each represents a hydrogen atom or an alkyl group and $R^4$ represents an alkyl group, by reacting a phenol, an alcohol and an aldehyde in the presence of a catalyst selected from the group consisting of a tertiary alkylamine, a tertiary unsubstituted benzylamine, a mixture of a tertiary alkylamine and a tertiary unsubstituted benzylamine, a carbonate of alkali metal, a hydrogencarbonate of alkali metal and a mixture of a carbonate of alkali metal and a hydrogencarbonate of alkali metal to form a reaction product; and recovering said alkoxyalkyl phenol from said reaction product.

2. A process for production of an alkoxyalkyl group substituted phenol according to claim 1 wherein the tertiary alkylamine is represented by the formula (2):

(2)

wherein $R^5$, $R^6$ and $R^7$ each represents an alkyl group of 1-20 carbon atoms and $R^5$, $R^6$ and $R^7$ may be identical or different, and the tertiary unsubstituted benzylamine is represented by the formula (3):

(3)

wherein $R^8$ and $R^9$ may be identical or different and each represents an alkyl group of 1-20 carbon atoms.

3. A process for production of an alkoxyalkyl group according to claim 2 wherein $R^5$, $R^6$, $R^7$, $R^8$ and $R^9$ each represents an alkyl group of 1-4 carbon atoms.

4. A process for production of an alkoxyalkyl group substituted phenol according to claim 1 wherein the tertiary alkylamine is at least one selected from the group consisting of triethylamine and trinormalbutylamine and the tertiary unsubstituted benzylamine is N,N-diethylbenzylamine.

5. A process for production of an alkoxyalkyl group substituted phenol according to claim 1 wherein the alkali metal is sodium or potassium.

6. A process for production of an alkoxyalkyl group substituted phenol according to claim 1 wherein the carbonate of alkali metal is at least one selected from the group consisting of sodium carbonate and potassium carbonate and the hydrogencarbonate is sodium hydrogencarbonate.

7. A process for production of an alkoxyalkyl group substituted phenol according to claim 1 wherein the phenol is represented by the formula (4):

(4)

wherein $R^1$ and $R^2$ each represents an alkyl group of 1-12 carbon atoms and $R^1$ and $R^2$ may be identical or different.

8. A process for production of an alkoxyalkyl group substituted phenol according to claim 1 wherein the phenol is 2,6-di-t-butylphenol.

9. A process for production of an alkoxyalkyl group substituted phenol according to claim 1 wherein the alcohol is represented by $R^4OH$ wherein $R^4$ is an alkyl group of 1-10 carbon atoms.

10. A process for production of an alkoxyalkyl group substituted phenol according to claim 9 wherein $R^4$ is an alkyl group of 1-4 carbon atoms.

11. A process for production of an alkoxyalkyl group substituted phenol according to claim 1 wherein the alcohol is methanol.

12. A process for production of an alkoxyalkyl group substituted phenol according to claim 1 wherein the aldehyde is paraformaldehyde.

13. A process for production of an alkoxyalkyl group substituted phenol according to claim 1 wherein amount of the aldehyde is 1-6 mols per 1 mol of the phenol.

14. A process for production of an alkoxyalkyl group substituted phenol according to claim 1 wherein the alcohol is used as a solvent.

15. A process for production of an alkoxyalkyl group substituted phenol according to claim 1 wherein reaction temperature at the reaction is 50°-250° C.

16. A process for production of an alkoxyalkyl group substituted phenol according to claim 1 wherein reaction temperature is 70°-150° C.

17. A process for production of an alkoxyalkyl group substituted phenol according to claim 1 wherein reaction pressure is 1-200 kg/cm².G.

18. A process for production of an alkoxyalkyl group substituted phenol according to claim 1 wherein reaction pressure is 5-100 kg/cm².G.

19. A process for production of an alkoxyalkyl group substituted phenol according to claim 1 wherein reaction time is 0.5-20 hours.

20. A process for production of an alkoxyalkyl group substituted phenol according to claim 1 wherein reaction time is 1-10 hours.

21. A process as claimed in claim 1 wherein said aldehyde is used in a proportion of about 2 to 4 moles per mole of said phenol.

22. A process as claimed in claim 1 including cooling said reaction product in an amount sufficient to crystallize said alkoxyalkyl ether therefrom, and separating said crystals therefrom.

23. A process as claimed in claim 1, wherein said reaction product comprises a mixture of solid and liquid and including separating said solids from said liquids; cooling said liquid in an amount sufficient to crystallize said alkoxyalkyl phenol, separating said crystals therefrom; admixing said separated solid with additional phenol, aldehyde, alcohol and catalyst; and again carrying out said reaction.

24. A process as claimed in claim 23 wherein said reaction is carried out at a temperature of about 20° to 125° C., at a pressure of about 1 to 200 kg/cm² and for a time of about 0.5 to 20 hours.

* * * * *

UNITED STATES PATENT AND TRADEMARK OFFICE
CERTIFICATE OF CORRECTION

PATENT NO.   :   4,952,736
DATED        :   August 28, 1990
INVENTOR(S)  :   Masahiro IWAHARA It is certified that error appears in the above-identified patent and that said Letters Patent is hereby corrected as shown below:

On the cover page, Item [73] "Idemitsu Petrochmeical" should read --Idemitsu Petrochemical--.

Signed and Sealed this

Fourteenth Day of January, 1992

Attest:

HARRY F. MANBECK, JR.

*Attesting Officer*          *Commissioner of Patents and Trademarks*